(12) United States Patent
Horn et al.

(10) Patent No.: US 8,481,139 B2
(45) Date of Patent: Jul. 9, 2013

(54) HIGH PERFORMANCE BALLOON CATHETER/COMPONENT

(75) Inventors: Daniel J. Horn, Shoreview, MN (US); Jeffrey S. Lindquist, Maple Grove, MN (US); Irina Nazarova, Woodbury, MN (US); Scott Schewe, Eden Prairie, MN (US); David W. Meister, Madison, WI (US); John J. Chen, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 279 days.

(21) Appl. No.: 12/637,490

(22) Filed: Dec. 14, 2009

(65) Prior Publication Data

US 2010/0094213 A1    Apr. 15, 2010

Related U.S. Application Data (63) Continuation of application No. 10/889,574, filed on Jul. 7, 2004, now Pat. No. 7,635,510.

(51) Int. Cl.
*B32B 23/00* (2006.01)
*B32B 1/08* (2006.01)

(52) U.S. Cl.
USPC ....... 428/36.1; 428/34.1; 428/34.2; 428/35.7; 428/35.9; 428/36.9

(58) Field of Classification Search
USPC .................. 428/34.1, 34.2, 35.7, 35.9, 36.1, 428/36.9
See application file for complete search history.

(56) References Cited

U.S. PATENT DOCUMENTS

| | | | |
|---|---|---|---|
| 3,023,982 A * | 3/1962 | Huch | 244/31 |
| 4,327,736 A | 5/1982 | Inoue | |
| 4,490,421 A | 12/1984 | Levy | |
| 4,706,670 A | 11/1987 | Andersen | |
| 4,808,465 A * | 2/1989 | Vane | 442/371 |
| 4,896,669 A | 1/1990 | Bhate et al. | |
| 4,906,244 A | 3/1990 | Pinchuk et al. | |
| 4,935,190 A | 6/1990 | Tennerstedt | |
| 4,950,239 A | 8/1990 | Gahara et al. | |
| 4,963,313 A | 10/1990 | Noddin et al. | |
| 5,026,607 A | 6/1991 | Kiezulas | |

(Continued)

FOREIGN PATENT DOCUMENTS

| | | |
|---|---|---|
| EP | 0553960 | 1/1993 |
| EP | 0540858 | 5/1996 |

(Continued)

OTHER PUBLICATIONS

Applicant's Statement re C.R. Bard Conquest Balloon.

(Continued)

*Primary Examiner* — Marc Patterson
(74) *Attorney, Agent, or Firm* — Vidas, Arrett & Steinkraus, P.A.

(57) ABSTRACT

Composite fiber reinforced balloons for medical devices prepared by applying a web of fibers to the exterior of a preformed underlying balloon and encasing the web with a matrix material to form a composite balloon. The fiber web is applied to at least the cone portion of the underlying balloon form. Either the cone portion of the underlying balloon form, or the web fibers applied to said cone portion, or both, have a friction-enhancing material coated thereon.

20 Claims, 6 Drawing Sheets

U.S. PATENT DOCUMENTS

| | | | |
|---|---|---|---|
| 5,096,848 A | 3/1992 | Kawamura | |
| 5,135,516 A | 8/1992 | Sahatjian et al. | |
| 5,201,706 A | 4/1993 | Noguchi et al. | |
| 5,250,069 A | 10/1993 | Nobuyoshi et al. | |
| 5,264,260 A | 11/1993 | Saab | |
| 5,270,086 A | 12/1993 | Hamlin | |
| 5,304,121 A | 4/1994 | Sahatjian | |
| 5,304,340 A | 4/1994 | Downey | |
| 5,306,246 A | 4/1994 | Sahatjian et al. | |
| 5,314,443 A | 5/1994 | Rudnick | |
| 5,328,468 A | 7/1994 | Kanekost et al. | |
| 5,330,428 A | 7/1994 | Wang et al. | |
| 5,330,429 A | 7/1994 | Noguchi et al. | |
| 5,344,400 A | 9/1994 | Kaneko et al. | |
| 5,403,340 A | 4/1995 | Wang et al. | |
| 5,407,623 A | 4/1995 | Zachariades et al. | |
| 5,500,180 A | 3/1996 | Anderson et al. | |
| 5,503,631 A | 4/1996 | Onishi et al. | |
| 5,509,899 A | 4/1996 | Fan et al. | |
| 5,556,383 A | 9/1996 | Wang et al. | |
| 5,576,072 A | 11/1996 | Hostettler et al. | |
| 5,578,374 A | 11/1996 | Dunbar et al. | |
| 5,647,848 A | 7/1997 | Jorgensen | |
| 5,693,034 A | 12/1997 | Buscemi et al. | |
| 5,702,756 A | 12/1997 | McKean et al. | |
| 5,714,110 A | 2/1998 | Wang et al. | |
| 5,797,877 A | 8/1998 | Hamilton et al. | |
| 5,827,289 A | 10/1998 | Reiley et al. | |
| 5,833,657 A | 11/1998 | Reinhardt et al. | |
| 5,868,708 A | 2/1999 | Hart et al. | |
| 5,913,861 A | 6/1999 | Trotta | |
| 5,958,582 A | 9/1999 | Dunbar et al. | |
| 6,110,483 A | 8/2000 | Whitbourne et al. | |
| 6,146,356 A | 11/2000 | Wang et al. | |
| 6,156,254 A | 12/2000 | Andrews et al. | |
| 6,267,775 B1 | 7/2001 | Clerc et al. | |
| 6,270,522 B1 | 8/2001 | Simhambhatla et al. | |
| 6,306,144 B1 * | 10/2001 | Sydney et al. | 606/108 |
| 6,416,494 B1 | 7/2002 | Wilkins | |
| 6,444,324 B1 | 9/2002 | Yang et al. | |
| 6,528,150 B2 | 3/2003 | Nazarova et al. | |
| 6,572,813 B1 | 6/2003 | Zhang et al. | |
| 6,673,053 B2 | 1/2004 | Wang et al. | |
| 6,695,809 B1 | 2/2004 | Lee | |
| 6,723,267 B2 | 4/2004 | Simmelink et al. | |
| 6,746,425 B1 * | 6/2004 | Beckham | 604/103.09 |
| 6,896,892 B2 * | 5/2005 | Mount et al. | 424/411 |
| 7,252,650 B1 | 8/2007 | Andrews et al. | |
| 7,635,510 B2 | 12/2009 | Horn et al. | |
| 2003/0054090 A1 | 3/2003 | Hansen | |
| 2003/0106346 A1 * | 6/2003 | Matsumoto | 66/195 |
| 2003/0139798 A1 | 7/2003 | Brown et al. | |
| 2004/0058603 A1 * | 3/2004 | Hayes | 442/286 |
| 2004/0082965 A1 | 4/2004 | Beckham | |
| 2004/0098120 A1 | 5/2004 | Williams et al. | |
| 2004/0109964 A1 | 6/2004 | Beckham | |

FOREIGN PATENT DOCUMENTS

| | | |
|---|---|---|
| EP | 1388346 | 2/2004 |
| EP | 1189553 | 3/2004 |
| WO | 9803218 | 1/1998 |
| WO | 2004028407 | 4/2004 |
| WO | 2004050140 | 6/2004 |

OTHER PUBLICATIONS

Database WPI; Section CH, Week 199537; Derwent Publications Ltd., London, GB; AN 1995-279974; XP002346900; & JP 07 178174 A (Terumo Corp); Jul. 18, 1995 abstract.

* cited by examiner

HIGH PERFORMANCE BALLOON CATHETER/COMPONENT

CROSS-REFERENCE TO RELATED APPLICATIONS

This application is a continuation of copending U.S. patent application Ser. No. 10/889,574 filed Jul. 7, 2004, which will issue as U.S. Pat. No. 7,635,510 on Dec. 22, 2009, the entire content of which is incorporated by reference herein.

BACKGROUND OF THE INVENTION

Medical devices comprising catheter shafts and catheter balloons are used in an increasingly widening variety of applications including vascular dilatation, stent delivery, drug delivery, delivery and operation of sensors and surgical devices such as blades, and the like. The desired physical property profile for the balloons used in these devices varies according to the specific application, but for many applications a high strength robust balloon is necessary and good softness and trackability properties are highly desirable.

Commercial high strength balloons having wall strengths in excess of 20,000 psi have been formed of a wide variety of polymeric materials, including PET, nylons, polyurethanes and various block copolymer thermoplastic elastomers. U.S. Pat. No. 4,490,421 Levy, and U.S. Pat. No. 5,264,260, Saab, describe PET balloons. U.S. Pat. No. 4,906,244, Pinchuk et al, and U.S. Pat. No. 5,328,468, Kaneko, describe polyamide balloons. U.S. Pat. No. 4,950,239, Gahara, and U.S. Pat. No. 5,500,180, Anderson et al describe balloons made from polyurethane block copolymers. U.S. Pat. No. 5,556,383, Wang et al, and U.S. Pat. No. 6,146,356, Wang et al, describe balloons made from polyether-block-amide copolymers and polyester-block-ether copolymers. U.S. Pat. No. 6,270,522, Simhambhatla, et al, describes balloons made from polyester-block-ether copolymers of high flexural modulus. U.S. Pat. No. 5,344,400, Kaneko, describes balloons made from polyarylene sulfide. U.S. Pat. No. 5,833,657, Reinhart et al, describes balloons having a layer of polyetheretherketone. All of these balloons are produced from extruded tubing of the polymeric material by a blow-forming radial expansion process. U.S. Pat. No. 5,250,069, Nobuyoshi et al, U.S. Pat. No. 5,797,877, Hamilton et al, and U.S. Pat. No. 5,270,086, Hamlin, describe still further materials which may be used to make such balloons.

A particular application which has a very high pressure requirement is reopening of stenoses which develop at or in long-term shunt, ports or grafts employed for repeated blood access, for instance with dialysis patients. Such stenoses are often highly calcified and essentially must be subjected to very high pressure for successful treatment. Moreover, frequently the vessels into which the access devices are connected are quite large. Consequently there is a need for balloons whose pressure profile allows for use of pressures in excess of 20 atm at balloon diameters which can exceed 5 mm.

Fiber reinforced balloons have been known for use in angioplasty and similar applications. U.S. Pat. No. 4,896,669, Behate, U.S. Pat. No. 4,706,670, Andersen, U.S. Pat. No. 5,647,848, Jorgensen, all show balloons formed with a fiber web reinforcement, but the rest condition of the balloon is straight. In some cases the balloon is a portion of the catheter tube in which a web pattern such as a braid has been modified to allow for elastic radial expansion to a diameter determined by the angle of the fiber reinforcements. The web is encased in an elastomeric polymer material.

U.S. Pat. Nos. 5,201,706, and 5,330,429, Noguchi, describe a laminate balloon which uses a release agent between a web layer and an inner layer of the balloon structure.

U.S. Pat. No. 5,827,289, Reiley, shows a mesh 170 "embedded or laminated and/or winding" used to form a neck on the balloon and a second mesh 170a used to form a tapered base. As understood, the mesh conforms the underlying balloon to the mesh shape, rather than conforming the mesh to a tapered section of a balloon.

U.S. Pat. No. 6,156,254, Andrews, shows a balloon formed by braiding fiber onto an unoriented tube and encasing the braid in same material; longitudinally stretching the braided tube onto a rod of smaller diameter; heating the tube ends, but not the middle; and then releasing the stretch force so the center recovers to formed diameter but the ends remain at the stretched diameter. The patent states that the fibers should be bonded to the wall material so that they do not move or slide significantly with respect to the wall material. Soft wall materials are described as balloon materials: polyurethane, SBS block copolymer, butadiene-acrylonitrile block copolymer. As an alternative, the inner tube layer may be PET or PVC, while the outer encasement material is polyurethane. In an alternative method of making the balloon, a polyurethane film is cast from dispersion onto an inflatable balloon form, the fiber braid is applied to the film layer and an outer layer of polyurethane is applied. The balloon is removed from the form by deflating the form.

SUMMARY OF THE INVENTION

The invention pertains to fiber reinforced laminate composite balloons and processes for preparing laminate composite balloons. In one such aspect, the balloon comprises a polymer material underlayer, an overlying fiber web/matrix material composite, wherein the fiber web material has a friction-enhancing material interposed at least between the underlayer and the fibers immediately adjacent thereto over a portion of the balloon that has a varying diameter. In another aspect, the balloon has an underlayer of a biaxially oriented polymer adheringly bonded to an overlying fiber web/matrix material composite. In yet another aspect, the balloon has an underlayer of a crosslinked polymer and an overlying fiber web/matrix material composite.

In some aspects the invention pertains to manufacturing processes for preparing composite fiber reinforced balloons by applying a web of fiber material to the exterior of a preformed underlayer balloon and encasing the web with a matrix material to form a composite balloon. In one such aspect, the invention pertains specifically to the step of applying a fiber web to a cone portion of an underlying balloon form. Either the underlying balloon form, or the web fibers applied to the cone portion, or both, have a friction-enhancing material applied thereto to reduce fiber slippage as it is applied to the cone portion. The friction reducing material may be a polymer coating or an adhesive.

In another such aspect, the invention pertains to a manufacturing method wherein the material of the polymeric balloon form, the fiber material and the matrix materials are mutually bonded to form a laminate composite balloon.

A still further aspect is a medical balloon comprising a styrene-isobutylene-styrene (SIBS) block copolymer, especially such a balloon which further comprises a reinforcing fiber web.

DETAILED DESCRIPTION OF THE INVENTION

Balloons of the invention are particularly suited to use in medical devices, for instance on balloon angioplasty catheters, in stent delivery systems, perfusion balloon devices, cutting balloon devices, cryoplasty devices, and the like. Typically they will be mounted on a catheter or probe device.

Referring to the drawing FIGS. 1-6, several aspects of the inventive processes are illustrated.

Figure 1:
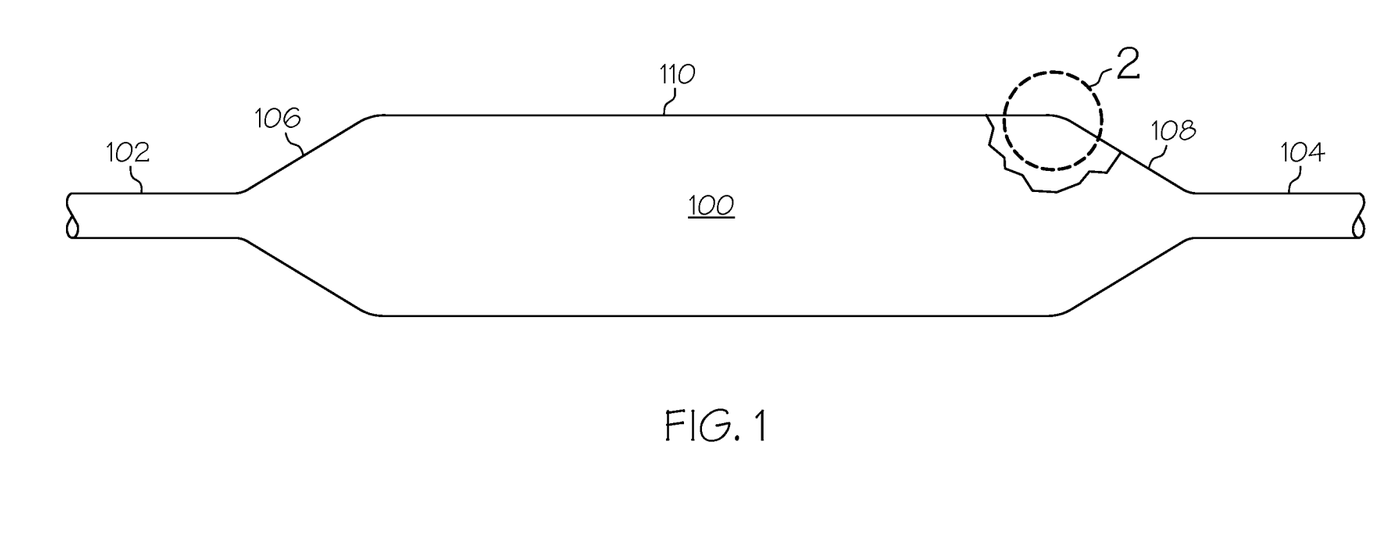
FIG. 1 is a schematic side view of an underlayer balloon with a partial cutaway.
Figure 2:
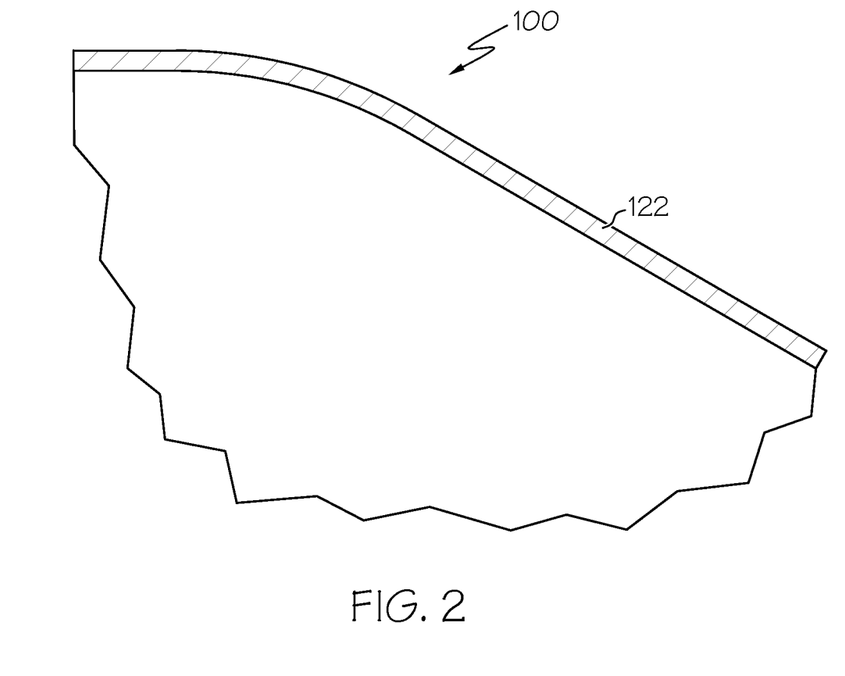
FIG. 2 is an enlarged cutaway view taken at line 2 of FIG. 1.

FIGS. 1 and 2 show an underlayer balloon 100 comprising waist regions 102, 104, cone regions 106, 108 and body region 110. The underlayer balloon is formed of a single layer 122 of a radially oriented thermoplastic polymer.

Figure 3:
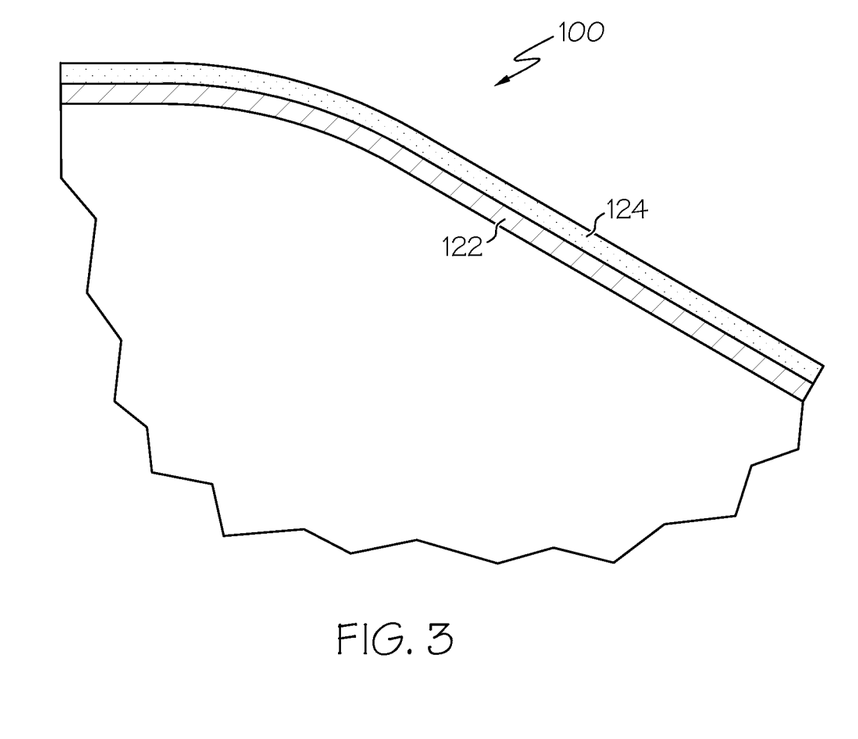
FIGS. 3-5 are views as in FIG. 2 illustrating steps of an embodiment of the inventive method.

FIG. 3 is a view as in FIG. 2, after a coating layer 124 of a friction-enhancing coating material has been applied to the underlayer balloon.

Figure 4:
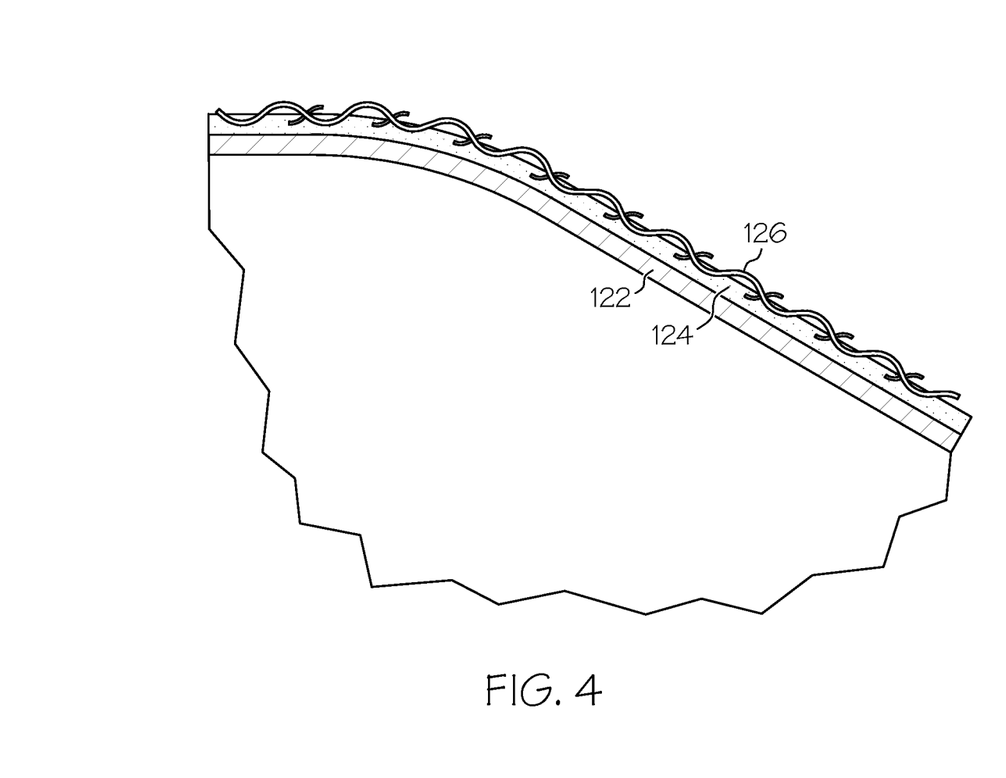

FIG. 4 is a view as in FIG. 3, after a fiber web 126 has been applied over the friction-enhancing coating 124.

Figure 5:
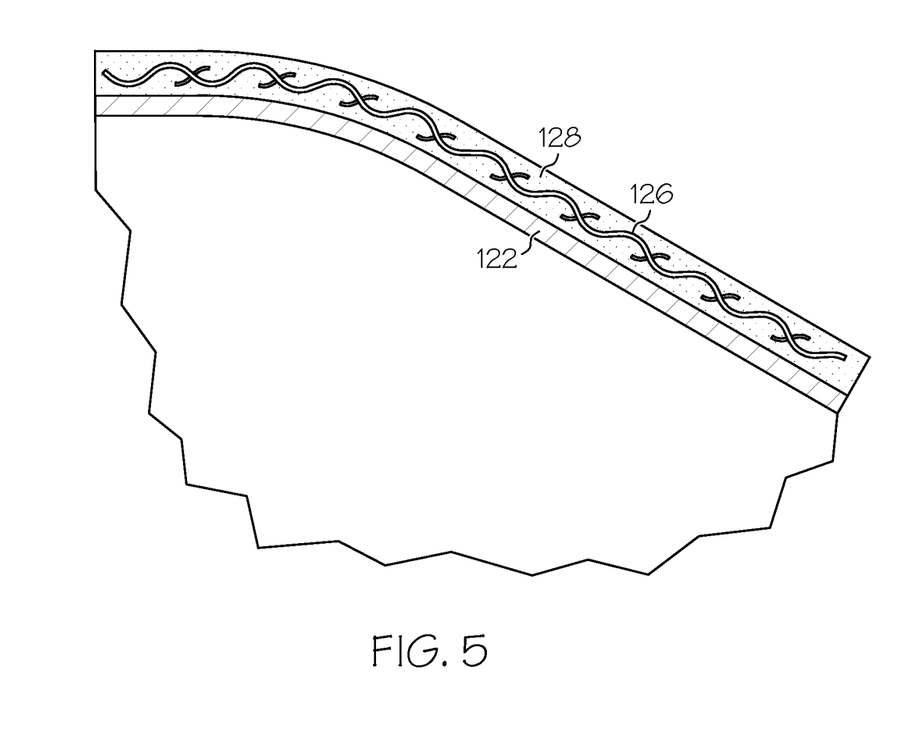

FIG. 5 is a view as in FIG. 4, after application of a matrix material which is the same as the friction-enhancing material. The web is encased in within the combined friction encasement/matrix 128.

Figure 6:
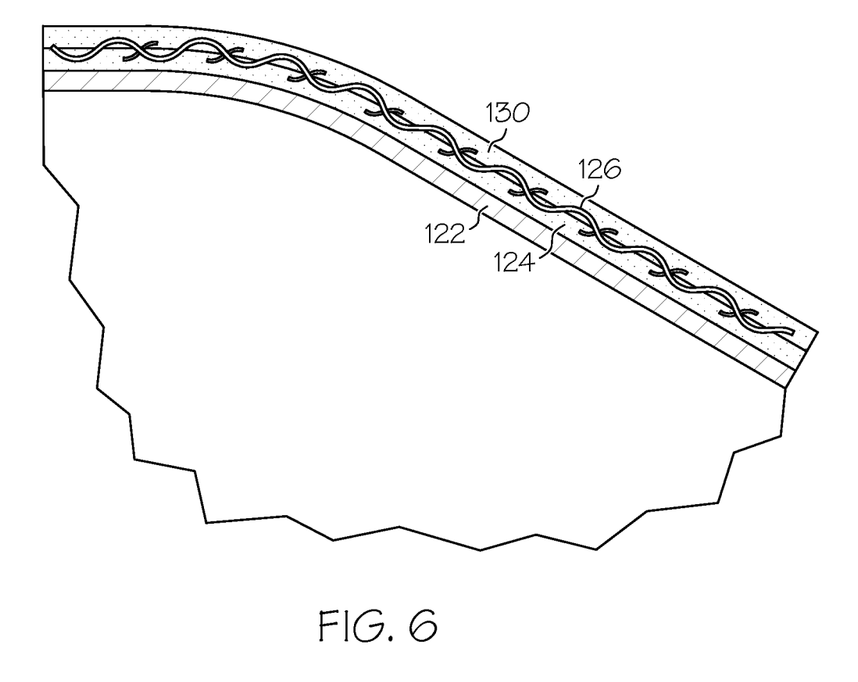
FIG. 6 is a view a balloon of the invention illustrating an alternate embodiment.

FIG. 6 is a view as in FIG. 4, after a matrix material 130, different from the friction-enhancing material, has been applied.

Underlayer Balloon

In some aspects the invention pertains to a composite balloon, or method of forming same, in which a web material is formed from fibers by application over an underlayer balloon form that becomes integrated into the composite balloon. The underlayer balloon has a rest state at ambient pressure (i.e. not pressurized) that includes cone portions. In the cone portions the diameter of the balloon varies, typically in a substantially continuous way.

The underlayer balloon may be preformed in a manner known for forming medical device balloons, for instance by radial expansion of a tubular parison, which is optionally also longitudinally stretched, of a semi-crystalline polymeric material to form the underlayer balloon or a preform balloon which is further processed into the underlayer balloon. The extruded parison may be radially expanded as is into a mold or by free-blowing. Alternatively, the parison may be pre-stretched longitudinally before expansion or reformed in various ways to reduce thickness of the balloon cone and waist regions prior to radial expansion. The blowing process may utilize pressurization under tension, followed by rapid dipping into a heated fluid; a sequential dipping with differing pressurization; a pulsed pressurization with compressible or incompressible fluid, after the material has been heated. Heating may also be accomplished by heating the pressurization fluid injected into the parison. Examples of these techniques may be found in the patent documents already mentioned or in U.S. Pat. No. 4,963,313, Noddin et al, U.S. Pat. No. 5,306,246 Sahatjian, U.S. Pat. No. 4,935,190, Tennerstedt, U.S. Pat. No. 5,714,110, Wang et al, U.S. Pat. No. 5,304,340, Downey. Various known methods of altering the properties of a radially expanded balloon such as heat-setting, heat shrinking, and/or radiation crosslinking may also be employed in forming the underlayer balloon. See U.S. Pat. No. 5,403,340, Wang et al; EP 540858, Advanced Cardiovascular Systems, Inc.; and WO 98/03218, Scimed Life Systems.

The underlayer balloon may be formed of any material which may be made by radial expansion of a tubular parison, typically thermoplastic polymers. Such materials may include low, linear low, medium and high density polyethylenes; polypropylenes; poly(ethylene vinyl acetate) (EVA); poly(ethylene vinyl alcohol) (EVOH) and EVA/EVOH terpolymers; polyolefin-ionomers; ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; polyesters and copolyesters; polycarbonate; thermoplastic elastomers; silicone-polycarbonate copolymers; polyamides; thermoplastic polyimides; liquid crystal polymers; ABS (acrylonitrile butadiene styrene); ANS (acrylonitrile styrene); Delrin polyacetal; PEI (polyetherimide); polyetheretherketone (PEEK) and PES (polyether sulfone). Physical blends and copolymers of such materials may also be used.

Orientable polymers are among the preferred materials for forming the underlayer balloon. Suitable orientable polymers include aromatic polyesters, especially polyethylene terephthalate (PET). PET polymers may have an initial intrinsic viscosity about 0.5 or more, for instance, 0.6-1.3. Other high strength polyester materials, such as poly(ethylene naphthalate) (PEN); and poly(butylene terephthalate) may also be used. Polyester copolymers incorporating ethylene terephthalate, ethylene naphthalate, butylene terephthalate and/or butylene naphthalate repeat units, may also be employed. Polyester copolymers such as the random copolymer made from dimethyl terephthalate dimethyl isophthalate and ethylene glycol described in U.S. Pat. No. 5,330,428 Wang, et al. may also be employed.

Examples of polyamides which may be used include nylon 6, nylon 64, nylon 66, nylon 610, nylon 610, nylon 612, nylon 46, nylon 9, nylon 10, nylon 11, nylon 12, and mixtures thereof.

The underlayer balloon may be formed of polyurethanes such as Tecothane® from Thermedics. Tecothane® is a thermoplastic, aromatic, polyether polyurethane synthesized from methylene diisocyanate (MDI), polytetramethylene ether glycol (PTMEG) and 1,4-butanediol chain extender. Tecothane® 1065D and 1075D are examples. Other polyurethanes that can be used include Isoplast® 301, a high strength engineering thermoplastic polyurethane, and Pellethane® 2363-75D, both sold by Dow Chemical Co. References illustrating polyurethane balloon materials include U.S. Pat. No. 4,950,239, to Gahara, U.S. Pat. No. 5,500,180 to Anderson et al, U.S. Pat. No. 6,146,356 to Wang, et al., and U.S. Pat. No. 6,572,813, to Zhang, et al.

Underlayer balloons may be also made of polyamide/polyether block copolymers. The polyamide/polyether block copolymers are commonly identified by the acronym PEBA (polyether block amide). The polyamide and polyether segments of these block copolymers may be linked through amide linkages, however, most preferred are ester linked segmented polymers, i.e. polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether.

Polyamide/polyether polyesters are sold commercially under the Pebax® trademark. Examples of suitable commercially available polymers are the Pebax® 33 series polymers with hardness 60 and above, Shore D scale, especially Pebax® 6333, 7033 and 7233. These polymers are made up of nylon 12 segments and poly(tetramethylene ether) segments linked by ester groups.

It is also possible to utilize polyester/polyether segmented block copolymers. Such polymers are made up of at least two polyester and at least two polyether segments. The polyether segments are the same as previously described for the polyamide/polyether block copolymers useful in the invention. The polyester segments are polyesters of an aromatic dicarboxylic acid and a two to four carbon diol.

The polyether segments of the polyester/polyether segmented block copolymers are aliphatic polyethers having at least 2 and no more than 10 linear saturated aliphatic carbon atoms between ether linkages. More preferably the ether segments have 4-6 carbons between ether linkages, and most preferably they are poly(tetramethylene ether) segments. Examples of other polyethers which may be employed in place of the preferred tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, preferably between 650 and 1000.

The polyester segments of the polyester/polyether segmented block copolymers are polyesters of an aromatic dicarboxylic acid and a two to four carbon diol. Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids. Preferred polyester/polyether block copolymers are poly(butylene terephthalate)-block-poly(tetramethylene oxide) polymers such as Arnitel® EM 740, sold by DSM Engineering Plastics, and Hytrel® polymers, sold by DuPont, such as Hytrel® 8230.

A suitable thermoplastic polyimide is described in U.S. Pat. No. 5,096,848 and is available commercially under the tradename Aurum® from Mitsui Toatsu Chemicals, Inc., of Tokyo, Japan.

Examples of liquid crystal polymers include the products Vectra® from Hoechst Celanese; Rodrun® from Unitika; LX and HX series polymers and Zenite™ polymers from DuPont; Sumikosuper™ and Ekonol™ from Sumitomo Chemical; Granlar™ from Grandmont; and Xydar® from Amoco. Suitably the liquid crystal polymer materials when employed in the underlayer balloon are blended with another thermoplastic polymer such as PET, nylon 12, or a block copolymer such as Pebax® 7033 or 7233 or Arintel® EM 740 or Hytrel 8230. The liquid crystal polymer may be present as filaments in a matrix of the blend polymer.

Alternatively, the underlayer balloon may be obtained by polymerization of a curable composition on a mold form, for instance as described in commonly owned copending application Ser. No. 10/662,621, filed Jul. 18, 2003.

The underlayer balloon is formed at a thickness which will provide a sufficiently rigid profile upon inflation to a low pressure, suitably 2-3 atm, to permit direct application of fibers thereto in a manner which forms a fiber web overlying the balloon. Preferably the underlayer balloon is substantially radially oriented or biaxially (radially and longitudinally) oriented. The underlayer balloon may have a wall thickness, single wall basis, of from about 5 μm to about 50 μm (0.0002-0.002 inches), preferably 10 to 30 μm (0.0004-0.0012 inches).

Fiber Web

Various techniques for forming webs are known. Suitable webs may be braids, weaves, mesh, helical windings, knits or random rovings. The web may be formed of different materials, for instance if anisotropic longitudinal lengthening and diameter expansion properties are desired.

The fiber selection and the web pattern can influence the distension properties of the composite balloon. Fiber tension during application to the underlayer balloon can also affect distension of the composite balloon, especially if elastomeric fibers are employed in whole or in part. In some preferred embodiments, however, the composite balloon is substantially non-distensible in both the longitudinal and radial directions, in which case the fibers have very low elongation, and the pattern is selected to provide minimal expansion. Weaves or braids are particularly desirable web-forms in these embodiments. A circular braider may be employed to apply the fibers to the underlayer balloon.

The web pattern may provide crossing fibers at any angle. Typically at least one set of the fibers will wind helically around the circumference of the underlayer balloon. In at least some embodiments a set of longitudinal fibers is provided, running parallel to the longitudinal axis over at least a portion of the underlayer balloon. The longitudinal fibers may be inelastic. In some embodiments the longitudinal fibers are interwoven or braided into the web pattern with fibers that wind helically around the balloon, for instance, the helical fibers may cross over and under the longitudinal fibers in an individually or grouped alternating fashion to provide the weave or braid. Crossing fibers that run at several different angles may be used. For instance, longtudinal fibers may be crossed both by fibers running at 45° and at 135° thereto. Particularly with fiber webs produced using mechanical braiders, crossing angles that produce optimal reinforcement may not occur with optimal gap spacing between fiber crossings. Groupings of individual fibers may be employed to reduce gap spacings at any desired crossing angle. For instance, crossing groupings of 2-6 fibers by 2-6 fibers may give better results than 1×1 crossings. The groupings may have different sizes, for instance 2 (longitudinal) by 4 (45° helical) by 4 (135° helical).

The fibers may be monofilament or multifilament fibers. Monofilament fibers are generally preferred. The fibers may range in size from 1 to 50 μm or in denier from 10-100, preferably 25-50. Moreover deviations from this size range can be achieved in some cases without departing from the invention.

Individual filaments in a multifilament fiber may have denier size less than 10 for instance from 1-5 denier. Larger filaments may also be employed in multifilament fibers. Multifilament fibers may be a blend of fibers of different materials.

The fiber material may be polyester, polyolefin, polyamide, polyurethane, liquid crystal polymer, polyimide, carbon, glass, mineral fiber or a combination thereof Polyesters include polyethyleneterephthalate (PET), polybutylene terephthalate (PBT), and polytrimethylene terephthalate (PTT). Polyamides include nylons and aramids such as Kevlar®. Liquid crystal polymers include Vectran®. Polyolefins include ultrahigh molecular weight polyethylene, such as Dyneema,® sold by DSM Dyneema BVm Heerlen, Netherlands, Spectra® fibers, sold by Honeywell, and very high density polyethylene, and polypropylene fibers. Elastomeric fibers can be used in some cases. In some specific embodiments of the invention, the fibers are high strength materials which have a very low elongation and creep, such as aramid, liquid crystal polymer, or ultrahigh molecular weight polyethylene described in U.S. Pat. Nos. 5,578,374, 5,958,582 and/or 6,723,267. Fibers comprising carbon nanotubes or carbon nano-fibers may be suitable. Other carbon materials may also be suitable in some applications.

Friction Enhancement

To facilitate integrity of the web applied to the cone portion of the underlayer balloon, a friction-enhancing material may be provided at the interface between the underlayer balloon and the web, at least over the cone portion. The web fibers may be coated with a friction-enhancing material, or a layer of friction-enhancing material may be applied to at least the cone portion of the underlayer balloon before application of the web fibers, or both. The friction enhancing material may also be provided at the interface between the underlayer balloon and the web over other portions of the balloon, for instance over the waist and/or body portions.

The friction-enhancing material may be a polymer that has a higher coefficient of friction than either or the underlayer balloon and the fiber and which is high enough that the fibers do not substantially slip off or around on the cone during web formation. Coefficient of friction is suitably determined per ASTM D3702 against a polished steel surface and values of about 0.7 or higher are recommended, especially about 0.8 and higher. Exemplary materials may be rubbery elastomeric thermoplastic polymers for instance, styrene-olefin block copolymers and acrylonitrile block copolymers. In some cases urethane-based thermoplastic elastomers, ester-based thermoplastic elastomers, olefin-based thermoplastic elastomers, and amide-based thermoplastic elastomers may be suitable. Linear low density polyethylene, very low density polyethylene, polyethylene-α-olefin copolymers or polycarbonate-urethane copolymers may be suitable in some cases.

One group of friction enhancers includes styrene-olefin thermoplastic elastomers. The styrene-olefin thermoplastic elastomer is a block copolymer having a soft segment and a hard segment within a molecule. The soft segment is a unit that is obtained from polymerization of an olefin, e.g., a polyisobutylene block, a polybutadiene block or a polyisoprene block. The component constituting the hard segment is a unit of styrene block, for example, that is obtained from a compound having one or at least two types selected from styrene and its derivatives, e.g., α.-methyl styrene, vinyl toluene, p-tertiary butyl styrene, 1,1-diphenyl ethylene and others.

Specific examples of the styrene-olefin thermoplastic elastomers.include: styrene-isobutylene-styrene block copolymer (SIBS); styrene-butadiene-styrene block copolymer (SBS); styrene-ethylene-butylene-styrene block copolymer (SEBS); styrene-isoprene-styrene block copolymer (SIS); styrene-ethylene-propylene-styrene block copolymer (SEPS); styrene-ethylene-ethylene-propylene-styrene block copolymer (SEEPS structure); and modified block copolymers thereof The content of styrene (or its derivatives) in each of the SIBS, SBS, SEBS, SIS, SEPS and SEEPS structures is preferably in a range of 10-50 wt. %, and more preferably in a range of 15-45 wt. % within the copolymer. A particular example is SIBS with about 17 wt % styrene.

The friction-enhancing coating material may also be an adhesive that is biocompatible when set. For instance, the adhesive may be one that provides at least some tack during application of the fibers. The adhesive may be a pressure sensitive, hot melt, solution, dispersion or curable material. In some embodiments of the invention, the adhesive will set up further after application of the fiber to provide a biocompatible adhering bond between the fibers and the balloon which is stronger than the initial tack adhesion. Partially cured radiation curable acrylate coating materials are exemplary.

The friction-enhancing coating may be applied from a solution or dispersion. In the case of a hot melt or curable adhesive, the coating may be applied neat. Suitable coating thicknesses are from about 1 to about 25 µm, for instance from about 2 µm to about 20 µm or from about 5 to about 10 µm.

Matrix

A polymeric matrix material is then applied over the web and over any exposed portions of the underlayer balloon to form the composite balloon. The matrix material should bind to the material that that is at least partially exposed to the matrix material under the particular technique employed. The exposed material may be one or more of the web fiber material, the friction-enhancing coating material, and the underlayer balloon. The matrix material may be the same or similar to the friction-enhancing material. The matrix material may also be the same or similar to the bulk material of the underlayer balloon, or it may be a wholly different material from both the friction-enhancing material and the underlayer balloon material. The matrix material may be one which provides a relatively low coefficient of friction, for instance about 0.6 or lower, especially about 0.5 and lower. Desirably the matrix material provides the composite balloon with an exterior which has good trackability, softness and low self adhesion ("non-blocking") after application.

The matrix material may be applied from solvent or dispersion. In some cases a curable liquid which sets up after application may be employed as matrix material. The matrix material may also be applied from the melt, for instance by spraying or extruding over the web.

Examples of matrix materials which may be employed include the styrene-olefin thermoplastic elastomers already described. Polyurethanes, for instance silicone modified polyurethanes may be employed. UV curable compositions as described in more detail below may also be employed.

In preferred embodiments the matrix material and the friction-enhancing material, in combination, also bind the filaments of the fibrous material to the underlayer balloon to a degree which is effective to substantially prevent loss of filament material into the body when the balloon is burst during use.

Composite Balloon

In addition to the components already described, the composite balloon may have a coating of a lubricous material or which comprises drug, as is generally known. See, for instance U.S. Pat. No. 5,135,516, Sahatjian, et al; U.S. Pat. No. 5,026,607, Kiezulas; U.S. Pat. No. 5,304,121, Sahatjian; U.S. Pat. No. 5,576,072, Hostettler, et al; U.S. Pat. No. 5,503,631, Onishi et al; U.S. Pat. No. 5,509,899, Fan et al; U.S. Pat. No. 5,693,034, Buscemi et al; U.S. Pat. No. 6,110,483, Whitbourne, et al; U.S. Pat. No. 5,702,756, Zhong; U.S. Pat. No. 6,528,150, Nazarova et al; and U.S. Pat. No. 6,673,053, Wang, et al. An anti-blocking coating material may also be employed to reduce self adhesion of the matrix material. In at least some cases anti-blocking and lubricity properties can be obtained with a single material, for instance a silicone fluid.

The composite balloon may have a single wall thickness of less than 115 µm (0.0045 inches), preferably less than 77 µm (0.003 inches). Suitably the single wall thickness is about 38 µm (0.0015 inches) or less, for instance about 25-35 µ(0.001-0.0014 inches).

Wall strengths for such balloons may be in excess of 15,000 psi (103,421 kPa), typically at least 18,000 psi (124,106 kPa), and in most cases in the range of about 20,000 (132,895 kPa) to 32,000 psi (220,632 kPa). Balloon diameters may range from about 1.5 to about 14 mm In use, it is often desirable to place a coating comprising a lubricious material, a medicament, or both, on the exterior surface of a medical device balloon. Such practice is also contemplated within the invention. However, if employed, such a coating is not considered to be part of the composite balloon structure for purposes of the claims presented herein.

The following examples illustrate the invention in preliminary, non-optimized trials.

EXAMPLE

Underlayer balloons were prepared by radial expansion of extruded tubes of Pebax® 7233 polymer. The underlayer balloons had an average double wall thickness in the body region of approximately 0.00252 inches (0.64 mm), a molded diameter of approximately 6 mm and a molded body length of approximately 2 cm. The underlayer balloons were sterilized with ethylene oxide according to a conventional protocol. At this stage, three balloons were retained, unbraided, as controls for comparison purposes.

The underlayer balloons were heat-sealed at their distal end. The proximal end was connected to a pneumatic syringe and pressurized balloon component to a firm stiffness (1-2 atm internal pressure).

A coating of SIBS polymer (17% isobutylene) was applied to the exterior surface of the underlayer balloon by hand dipping the pressurized balloon component into a 1% solution of the SIBS polymer in toluene, drawing the balloon component out of solution and allowing it to dry.

A braiding machine was utilized to weave a web of fibers of 55 denier Kevlar® aramid around the inflated balloon components. Speeds were adjusted as braiding progressed in a manner directed to achieve a single layer light braiding (5 balloons) (estimated about 30-50% surface coverage) or a single layer heavy braiding as tightly as possible (5 balloons) (estimated 91% fiber coverage).

Close attention was paid to braiding in the region of the balloon cones. These were positions where the fibers had a tendency to slip. When an attempt to lightly weave fibers on an underlayer balloon that had not been coated with the SIBS layer was made, the fibers slipped and bunched up over the waist region of the balloon when application to the cone was attempted. By contrast, an excellent result obtained when a SIBS coated underlayer balloon was used.

After the Kevlar® fiber web had been applied, a secondary SIBS coating (matrix) was produced by again dipping the pressurized balloon component into a 1% solution of the SIBS polymer in toluene, drawing the balloon component out of solution and letting it thoroughly dry.

Uncoated balloon components were retained as controls. The controls were inflated but received neither the SIBS coatings nor braiding.

The balloons were deflated, by cutting one sealed end, and the double wall thickness was measured. Double wall thicknesses of the final braided balloons were: approximately 0.0042 inches (107 nm) for the light braid—and approximately 0.0068 inches (173 µm) for the heavy braid. The balloons were then attached to burst machines, and inflated in a 37° C. water bath. The balloon was pressurized at 1 atm increments until burst. Measured burst pressures were 22-25 atm for the unbraided controls, 30 atm for the light braid and 34-35 atm for the heavy braid.

Longitudinal growth over the range 4-15 atm was 15.5% for the control versus only 3% for the heavy braid balloon.

Curable Material

As previously described, the invention may use a liquid composition which is curable to a solid polymer. Such a material may be employed to form the underlayer balloon, the friction enhanced interface, the matrix or any combination thereof Radiation curing compositions of (meth)acrylate esters (i.e. acrylates, methacrylates and mixtures thereof) are well known and may be used in the invention. A wide variety of cured properties are available from such compositions. Unless e-beam sources are used, such compositions typically employ a photoinitiator.

The radiation curable compounds, such as those which are initiated with UV or visible light radiation, may be monomeric, oligomeric, prepolymeric, or polymeric in nature. Mixtures of such compounds are typically used. Typically the compositions are liquids prior to curing in order facilitate application of the composition, and then cure to a crosslinked solid after being exposed to radiation such as UV or visible light radiation.

Examples of (meth)acrylate terminated radiation curable compounds include, but are not limited to, epoxy (meth)acrylates, urethane (meth)acrylates (aliphatic and aromatic), polyester (meth)acrylates, acrylic (meth)acrylates, polycarbonate (meth)acrylates and so forth and mixtures thereof Other suitable UV curable compositions include cationically polymerizable compounds, most notably epoxies. Examples of commercially available suitable UV curable epoxies include, but are not limited to, UVACURE® 1500, 1530 and 1534 available from UCB Radcure, SARCAT® K126 available from Sartomer, and so forth. Vinyl ethers and styryloxy ethers are other cationically polymerizable compounds which can be used.

Another type of formulation which may be utilized in the invention is a photo-activated Diels-Alder addition reaction of an aromatic 2,5-dialkyl-1,4-diketone and a compound having two or more (meth)acrylate or maleimide groups thereon, optionally with a chain terminating mono-maleimide, or (meth)acrylate.

As an alternative to radiation curing, a composition which is curable upon mixing of two or more components may be employed, the individual components being stable until mixed. The individual components may be blended on-the-fly, so that the resulting composition cures promptly as it is applied, but does not cure in the application apparatus.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim, if such multiple dependent format is an accepted format within the jurisdiction. In jurisdictions where multiple dependent claim formats are restricted, the following dependent claims should each be also taken as alternatively written in each singly dependent claim format which creates a dependency from a antecedent-possessing claim other than the specific claim listed in such dependent claim below.

The invention claimed is:

1. A fiber reinforced laminate composite balloon, the balloon is a medical balloon, the balloon comprising a preformed underlying balloon layer having a cone region, a fiber web disposed over the underlying balloon layer at least over said cone portion, and a matrix material encasing the web, and a friction-enhancing material disposed only on the cone portion of the underlying balloon layer.

2. A fiber reinforced laminate composite balloon as in claim 1 wherein the friction-enhancing material has a coefficient of friction of about 0.7 or more.

3. A fiber reinforced laminate composite balloon as in claim 1 wherein the friction-enhancing material is an elastomeric polymer.

4. A fiber reinforced laminate composite balloon as in claim 1 wherein the friction-enhancing material is an adhesive.

5. A fiber reinforced laminate composite balloon as in claim 1 wherein the polymer underlayer is formed by radial expansion of a tubular parison.

6. A fiber reinforced laminate composite balloon as in claim 1 wherein the polymer underlayer is radially and longitudinally oriented.

7. A fiber reinforced laminate composite balloon as in claim 1 wherein the fibers have a diameter of from 1 to 50 μm.

8. A fiber reinforced laminate composite balloon as in claim 1 wherein the fibers are in the range of from about 10 to about 100 denier.

9. A fiber reinforced laminate composite balloon as in claim 1 wherein fiber material is selected from the group consisting of polyester, polyolefin, polyamide, polyurethane, liquid crystal polymer, polyimide, carbon, glass, mineral fiber or a combination thereof.

10. A fiber reinforced laminate composite balloon as in claim 1 wherein the matrix material is an elastomeric polymer.

11. A fiber reinforced laminate composite balloon as in claim 1 wherein said friction enhancing material is a styrene-isobutylene-styrene block copolymer.

12. A medical device comprising a balloon as in claim 1 mounted on a catheter or probe.

13. The fiber reinforced laminate composite balloon of claim 1, the underlying balloon layer comprising a crosslinked polymer.

14. The fiber reinforced laminate composite balloon of claim 4 wherein the adhesive is tacky and is set to form a stronger bond at a time subsequent to applying the fibers to the underlying balloon.

15. The fiber reinforced laminate composite balloon of claim 1 wherein the fiber web comprises at least one material selected from the group consisting of aramid, ultrahigh molecular weight polyolefin, liquid crystal polymer and mixtures thereof.

16. The fiber reinforced laminate composite balloon of claim 1 wherein the matrix material is an elastomeric polymer.

17. The fiber reinforced laminate composite balloon of claim 1 wherein said balloon is formed of polymer material styrene-isobutylene-styrene block copolymer.

18. The fiber reinforced laminate composite balloon of claim 1 wherein the balloon has a longitudinal axis and the fiber web comprises longitudinal fibers extending in a direction generally parallel to the longitudinal axis and helically extending fibers intermittently crossing over and under the longitudinal fibers at least at one crossing angle.

19. The fiber reinforced laminate composite balloon of claim 1 wherein the fiber web comprises fibers braided or woven with fibers running in at least two directions to provide fiber crossings at one or more crossing angles, wherein for at least one said fiber direction two or more fibers are grouped together in each crossing.

20. A fiber reinforced laminate composite balloon, the balloon is a medical balloon, the balloon having a length and including a portion along the length of the balloon that has a varying diameter, the balloon comprising a polymer underlayer, and an overlying fiber web/matrix material composite, wherein a friction-enhancing material is interposed at least between the underlayer and the fibers immediately adjacent thereto over only the portion of the balloon that has a varying diameter.

* * * * *